US00PP15192P2

(12) United States Plant Patent
Slaughter et al.

(10) Patent No.: US PP15,192 P2
(45) Date of Patent: Sep. 28, 2004

(54) NECTARINE TREE, 'BURNECTFOURTEEN'

(50) Latin Name: *Prunus persica*
Varietal Denomination: Burnectfourteen

(75) Inventors: John K. Slaughter, Clovis, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 10/738,760

(22) Filed: Dec. 16, 2003

(51) Int. Cl.[7] ..... A01H 5/00
(52) U.S. Cl. ..... Plt./188
(58) Field of Search ..... Plt./188

*Primary Examiner*—Kent Bell
*Assistant Examiner*—S. B. McCormick-Ewoldt
(74) *Attorney, Agent, or Firm*—Wells St. John P.S.

(57) ABSTRACT

A new and distinct variety of nectarine tree (*Prunus persica* sub species *nuciperisica*), denominated varietally as 'Burnectfourteen', and which produces an attractively colored white-fleshed, non-melting, sub-acid clingstone nectarine, which is mature for harvesting and shipment approximately May 15 to May 24 under ecological conditions prevailing in the San Joaquin Valley of central California.

1 Drawing Sheet

BACKGROUND OF THE NEW VARIETY

The present invention relates to a new, novel and distinct variety of nectarine tree, *Prunus persica* (subspecies *nucipersica*), which has been denominated varietally as 'Burnectfourteen.'

The present variety of nectraine tree resulted from an on-going program of fruit and nut tree breeding. The purpose of this program is to improve the commercial quality of available deciduous fruit and nut varieties, and rootstocks, by creating and releasing promising selections of prunus, malus and regia species. To this end we make both controlled and hybrid cross pollinations each year in order to produce seedling populations from which improved progenies are evaluated and selected.

The seedling 'Burnectfourteen' was originated by us from a population of seedlings grown in our experimental orchards located near Fowler, Calif. The seedlings, grown on their own roots, were the result of a controlled cross of the yellow-fleshed 'Crimson Baby' nectarine tree (non-patented), which was used as the seed parent; and a sub-acidic white-fleshed, non-melting, nectarine tree of unknown parentage which was used as the pollen parent. One seedling, which is the present variety, exhibited especially desirable characteristics, and was marked for subsequent observation. After the 1998 fruiting season, the new, present variety, was selected for advanced evaluation and repropagation.

ASEXUAL REPRODUCTION

Asexual reproduction of the new and distinct variety of nectarine tree was accomplished by budding the new nectarine tree to 'Nemaguard' Rootstock (non-patented). This was performed by us in our experimental orchard which is located near Fowler, Calif. Subsequent evaluations have shown those asexual reproductions run true to the original tree. All characteristics of the original tree, and its fruit, were established, and appear to be transmitted through succeeding asexual propagations. We have observed fruit for the past 4 successive years from approximately 15 propagated trees.

SUMMARY OF THE VARIETY

'Burnectfourteen' is a new and distinct variety of nectarine tree, which is considered of large size, and which has vigorous growth. This new nectarine tree variety is also a regular and productive bearer of relatively large, firm, sub-acidic white fleshed, non-melting, clingstone fruit which have good flavor and eating quality. The tree of the present variety displays a medium low high chilling requirement of approximately 375 hours. Still further, the present tree also produces relatively uniformly sized fruit throughout the tree. Additionally, the fruit produced by the present tree has a high degree of red skin coloration, a firm flesh and appears to have good handling and shipping qualities. The 'Burnectfourteen' Nectarine tree bears fruit which are ripe for commercial harvesting and shipment on approximately May 15 to May 23 under the ecological conditions prevailing in the San Joaquin Valley of central California. In relative comparison to the pollen parent, the 'Burnectfourteen' Nectarine ripens 7 to 10 days later. Further when contrasted to the seed parent 'Crimson Baby', 'Burnectfourteen' produces a white fleshed and sub-acidic fruit.

BRIEF DESCRIPTION OF THE DRAWINGS

The accompanying drawing, which is provided is a color photograph of the new variety of nectarine tree. The photograph depicts two whole mature fruit, and one mature fruit is dissected substantially in the equatorial plane, viewed from the apical perspective, and which reveals the flesh and the stone characteristics thereof. The external coloration of the fruit, as shown, is sufficiently matured for harvesting and shipment. Additionally, the photograph displays a sample vegetative shoot bearing typical leaves, and a typical stone, with the fleshed removed. The colors in the photograph are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society) and descriptions provided.

DETAILED DESCRIPTION

Referring more specifically to the pomological details of this new and distinct variety of nectarine tree, the following has been observed during the fourth fruiting season under the ecological conditions prevailing at orchards located near the town of Fowler, county of Fresno, state of Calif. All major color code designations are by reference to The RHS Colour Chart (Fourth Edition) provided by The Royal Horticultural Society of Great Britain. Common color names are also occasionally used.

TREE

Size: Generally.—Considered medium-large as compared to other common commercial nectarine cultivars ripening in the early season of maturity. The tree of the present variety was pruned to a height of approximately 270.0 cm to about 300.0 cm at maturity.

Vigor: Considered vigorous. The present variety grew from about 161.0 cm to 178.0 cm in height during the first growing season. The new nectarine tree variety was pruned to a height of approximately 150.0 cm during the first dormant season, and primary scaffolds were then selected for desired tree structure.

Productivity: Productive. Fruit set varies from 2.0 to several times more than the desired crop load. Fruit set is spaced by thinning to develop the remaining fruit into the desired market sized fruit. The number of the fruit set varies with prevailing climatic conditions, and the cultural practices employed during the bloom period, and is therefore not distinctive of this new variety.

Bearer: Regular. Fruit set has been heavy, and thinning was necessary during the past 4 years.

Form: Upright, and pruned to a vase shape.

Density: Considered medium dense. It has been discovered that pruning the branches from the center of the tree to obtain a resulting vase shape allows for proper air movement in the tree, and appropriate amounts of sunlight to enhance fruit color and renewal of fruiting wood throughout the tree.

Hardiness: The present tree was grown and evaluated in USDA Hardiness Zone 9. Winter chilling requirements of the new tree are approximately 375 hours below 7.0 degrees C. The variety appears to be hardy under typical Central San Joaquin Valley climatic conditions.

TRUNK

Diameter: Approximately 14.0 cm in diameter when measured at a distance of approximately 15.24 cm above the soil level, at the end of the fourth growing season.

Bark Texture: Considered moderately rough, with numerous folds of papery scarfskin being present.

Lenticels: Numerous flat, oval lenticels are present. The lenticels range in size from approximately 4.0 to about 9.0 millimeters in width, and from about 1.0 to about 2.0 millimeters in height.

Lenticel color: Considered an Orange Brown, (RHS Greyed-Orange Group 166 C).

Bark coloration: Variable, but it is generally considered to be gray-brown, (RHS Greyed-Orange Group 177 A).

BRANCHES

Size: Considered medium for the variety.

Diameter: Average as compared to other nectarine tree varieties. The branches have a diameter of about 6.8 centimeters when measured during the fourth year after grafting.

Surface texture: Average, and appearing furrowed on wood which is several years old.

Crotch angles: Primary branches are considered variable between about 46 to about 53 degrees from the horizontal axis. The particular characteristic is not considered distinctive of the variety, however.

Current season shoots: Surface texture—Substantially glabrous.

Internode length: Approximately 2.5 to about 2.8 cm. This tree characteristic is highly dependent upon plant nutrition, soil quality, pruning and tree care and therefore is not distinctive of the variety.

Color of mature branches: Medium brown, (RHS Greyed-Orange 174 A).

Current seasons shoots: Color.—Light green, (RHS Yellow-Green Group 144 C). The color of new shoot tips is considered a bright and shiny green (RHS Green Group 139 B).

LEAVES

Size: Considered medium for the species. Leaf measurements have been taken from vigorous, upright, current-season growth, at approximately mid-shoot.

Leaf length: Approximately 132.0 to about 150.0 millimeters.

Leaf width: Approximately 34.0 to about 38.0 millimeters.

Leaf base shape: Slightly oblique relative to the leaf longitudinal axis.

Leaf form: Lancelolate.

Leaf tip form: Acuminate.

Leaf color: Upper Surface—Dark green, (approximately RHS Green Group 137 A).

Leaf texture: Glabrous.

Leaf color: Lower Surface.—Medium green, (RHS Green Group 139 B).

Leaf venation: Pinnately veined.

Mid-vein. Color.—Light yellow green, (RHS Yellow-Green Group 150 D).

Leaf margins.—Slightly undulating.

*Form.*—Considered crenate, occasionally doubly crenate.

*Uniformity.*—Considered generally uniform.

Leaf petioles:

*Size.*—Considered medium long.

*Length.*—About 6.0 to about 9.0 mm.

*Diameter.*—About 2.0 to about 2.5 mm.

*Color.*—Pale green, (RHS Yellow Group 150 C).

Leaf glands:

*Size.*—About 1.0 mm in height and about 1.0 mm in width.

*Number.*—Generally one per side, occasionally two per side.

*Type.*—Globose, considered reasonably unappressed to the petiole margin and moderately small. The glands on more mature leaves are occasionally senescent. The leaves are early deciduous.

*Color.*—Orange brown, (RHS Grey-Brown Group N199 C).

Leaf stipules:

*Size.*—Medium for the variety.

*Number.*—Typically 2 per leaf bud and up to 6 per shoot tip.

*Form.*—Lanceolate in form, and having a serrated margin.

*Color.*—Green, (RHS Green Group 141 B) when young, but graduating to a brown color, (RHS Greyed-Orange group 165 A) with advancing senescence. The stipules are considered to be early deciduous.

FLOWER

Flower buds: Generally—The floral buds, depending upon stage of development, are approximately 8.0 millimeters wide; and about 13.0 millimeters long; conic in form; and slightly appressed relative to the bearing shoot.

Flower buds: Color—The bud scales are reddish-brown, (approximately RHS Greyed Purple Group 183 A). The buds are considered hardy under typical central San Joaquin Valley climate conditions.

Hardiness: No winter injury has been noted during the last several years of evaluation in the central San Joaquin Valley. The current variety has not been intentionally subjected to drought or heat stress, and therefore this information is not available.

Date of first bloom: Feb. 19, 2003.

Blooming time: Considered early mid-season in relative comparison to other commercial nectarine cultivars grown in the central San Joaquin Valley. Date of full bloom was observed on Feb. 23, 2003. The date of bloom varies slightly with the prevailing climatic conditions, and cultural practices.

Duration of bloom: Approximately 10 days. This characteristic varies slightly with climatic conditions.

Flower type: The variety is considered to have a showy type flower.

Flower size: Flower diameter at full bloom is approximately 42.0 to about 47.0 millimeters.

Bloom quantity: Considered very abundant.

Flower bud frequency: Normally 1 to 2 flower buds appear per node. Rarely 3 buds per node may be observed.

Petal size: Generally—Considered large for the species.

*Length.*—Approximately 19.0 to about 22.0 millimeters.

*Width.*—Approximately 17.0 to about 21.0 millimeters.

Petal form: Rotund.

Petal count: Generally 5. Occasionally individual flower pedal counts are doubled.

Petal texture: Glabrous.

Petal color: Light pink, (RHS Red-Purple Group 62 B) to a medium pink, (RHS Red-Purple Group 63 C).

Fragrance: Slight.

Petal claw:

*Form.*—The claw is considered truncate in shape, and has a large size when compared to other varieties.

*Length.*—Approximately 7.0 to about 10.0 millimeters.

*Width.*—Approximately 7.0 to about 8.0 millimeters.

Petal margins: Generally considered variable, from nearly smooth, to moderately undulate.

Petal apex: Generally—The petal apices generally appear entire and without an apical groove.

Flower pedicel:

*Length.*—Considered medium-long, and having an average length of approximately 4.0 to about 5.0 millimeters.

*Diameter.*—Considered average, approximately 2.0 millimeters.

*Color.*—A pale green, (RHS Greyed Green Group 195 A).

Floral nectaries:

*Color.*—A pale greenish brown, (RHS Greyed-Green Group 197 B).

Calyx:

*Surface texture.*—Generally glabrous.

*Color.*—A dull red, (approximately RHS Greyed-Purple Group 187 B).

Sepals:

*Surface texture.*—The surface has a short, fine, pubescent texture.

*Size.*—Average, and ovate in form.

*Color.*—A dark reddish purple, (approximately RHS Greyed-Purple Group 187 C).

Anthers:

*Generally.*—Large in size.

*Color.*—Red to reddish purple, (approximately RHS Greyed-Purple Group 187 D).

Pollen production: Pollen is abundant, and has a yellow color, (approximately RHS Yellow Group 11 A).

Filaments:

*Size.*—Variable in length, approximately 15.0 to about 19.0 millimeters in length.

*Color.*—Considered a pale pink, (RHS Red-Purple Group 65 C).

Pistil:

*Number.*—Usually 1, occasionally 2.

*Generally.*—Average in size.

*Length.*—Approximately 17.0 to about 20.0 millimeters including the ovary.

*Color.*—Considered a very pale green, (approximately RHS Yellow-Green Group 145 C).

*Surface texture.*—The variety has a long glabrous pistil.

FRUIT

Maturity when described: Firm ripe condition (shipping ripe). Date of first picking.—May 15, 2003. Date of last picking.—May 24, 2003. The date of harvest varies slightly with climatic conditions.

Size: Generally—Considered relatively large, and uniform.

Average cheek diameter: Approximately 70.0 to about 75.0 millimeters.

Average axial diameter: Approximately 68.0 to about 71.0 millimeters.

Typical weight: Approximately 215.0 grams. This characteristic is highly dependent upon cultural practices, and therefore is not particularly distinctive of this new variety.

Fruit form: Generally—Rounded. The fruit is generally uniform in symmetry with an occasional extension in the sutorial plane.

Fruit suture: Shallow, and extending from the base to apex. No apparent callousing or stitching exists along the suture line.

Suture: Color—The background color appears to be white, (approximately RHS White Group 155 C), with occasional red coloration, (approximately RHS Red Group 46 C).

Ventral surface: Form—Full, to slightly extended.

Apex: Rounded.

Base: Retuse.

Stem cavity: Rounded and relatively shallow. The average depth of the stem cavity is about 1.45 cm. The average width of the stem cavity is about 1.64 cm.

Fruit skin:

*Thickness.*—Considered medium in thickness, and tenacious to the flesh.

*Texture.*—Glabrous.

*Taste.*—Non-astringent.

*Tendency to crack.*—A rare incidence of cracking has been observed. Occasional russeting can be observed in some years.

Color:

*Blush color.*—The blush color is variable from a medium red, (approximately RHS Red Group 44 A) to a dark red, (approximately RHS Red-Purple Group 59 A). Blush color ranges from 75% to about 95% of the fruit surface depending upon the sunlight exposure and prevailing growing conditions.

*Ground color.*—Generally a light yellow, (approximately RHS White Group 155 C).

Fruit stem: Moderate in length, approximately 5.0 to about 7.0 millimeters.

*Diameter.*—Approximately 2.0 to about 3.0 millimeters.

*Color.*—Light tan, (approximately RHS Greyed-Orange Group 164 D).

Flesh:

*Ripens.*—Evenly.

*Texture.*—Firm, and dense. Considered non-melting.

*Fibers.*—Few, small, and tender ones are found.

*Aroma.*—Slight.

*Eating quality.*—Considered very good.

*Flavor.*—Considered sweet and sub-acidic. The flavor is considered pleasant.

*Juice.*—Moderate.

*Brix.*—About 17.5 degrees. This characteristic varies slightly with the number of fruit per tree; the prevailing cultural practices; and the surrounding climatic conditions.

*Flesh color.*—Pale white, (approximately RHS White Group 155 C).

STONE

Type: Clingstone.

Size: Considered medium for the variety. The stone size varies with the resulting crop load, and tree vigor, and is therefore is not considered a distinguishing characteristic of this new variety.

Length: Average, about 23.5 to about 27.0 millimeters.

Width: Average, about 22.0 to about 24.0 millimeters.

Diameter: Average, about 16.0 to about 21.0 millimeters.

Form: Obovoid.

Base: The stone is usually oblique relative to the stone's vertical axis.

Apex: Shape.—The stone apex has a raised tip.

Stone surface:

*Surface texture.*—The surface texture is characterized generally by a concentric ridge/furrow pattern which begins at the margins. Substantial grooving over the apical shoulders is evident. Surface pitting is less generally noted than ridges or furrows, but is more frequently observed in the mid-section of the stone. Substantial erosion is usually observed along the pit margin near the tip and on the ventral side.

*Ridges.*—The surface texture varies from sharp to rounded.

*Ventral edge.*—Width — Considered medium, and having a dimension of approximately 2.0 to about 4.0 millimeters when measured at the mid-suture. The wings are most prominent over the suture line.

*Dorsal edge.*—Shape. — Full, heavily grooved, and having relatively smooth edges.

Stone color: The color of the dry stone is a pale orange (Greyed-Orange Group approximately RHS 170 C).

Tendency to split: Occasional splits have been noted.

Kernel: Generally—The kernel is considered immature and semi-gelatinous.

*Form.*—Considered ovoid.

*Pellicle.*—Pubescent.

*Color.*—Considered to be a pale brown (Yellow-White Group 158 A).

Use: The subject variety 'Burnectfourteen' is considered to be a Nectarine tree which matures early in the season, and which produces fruit, which are considered firm, attractively colored, and which are useful for both local and long distance shipping.

Keeping quality: Excellent. Fruit has stored well for up to 25 days after harvest at 1.0 degree Celsius.

Shipping quality: Good. The fruit of the new nectarine tree variety showed minimal bruising of the flesh, or skin damage, after being subjected to normal harvest and packing procedures.

Resistance to insects and disease: No particular susceptibilities were noted. The present variety has not been tested to expose or detect any susceptibilities or resistances to any known plant and/or fruit diseases.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety nectarine tree, what we claim is new and desire to secure by Plant Letters Patent is:

1. A new distinct variety of nectarine tree, substantially as illustrated and described, and which is characterized principally as to novelty by producing an attractively colored, white-fleshed, non-melting, sub-acid clingstone nectarine which is mature for harvesting and shipment approximately May 15 to May 24 under the ecological conditions prevailing in the San Joaquin Valley of central Calif.

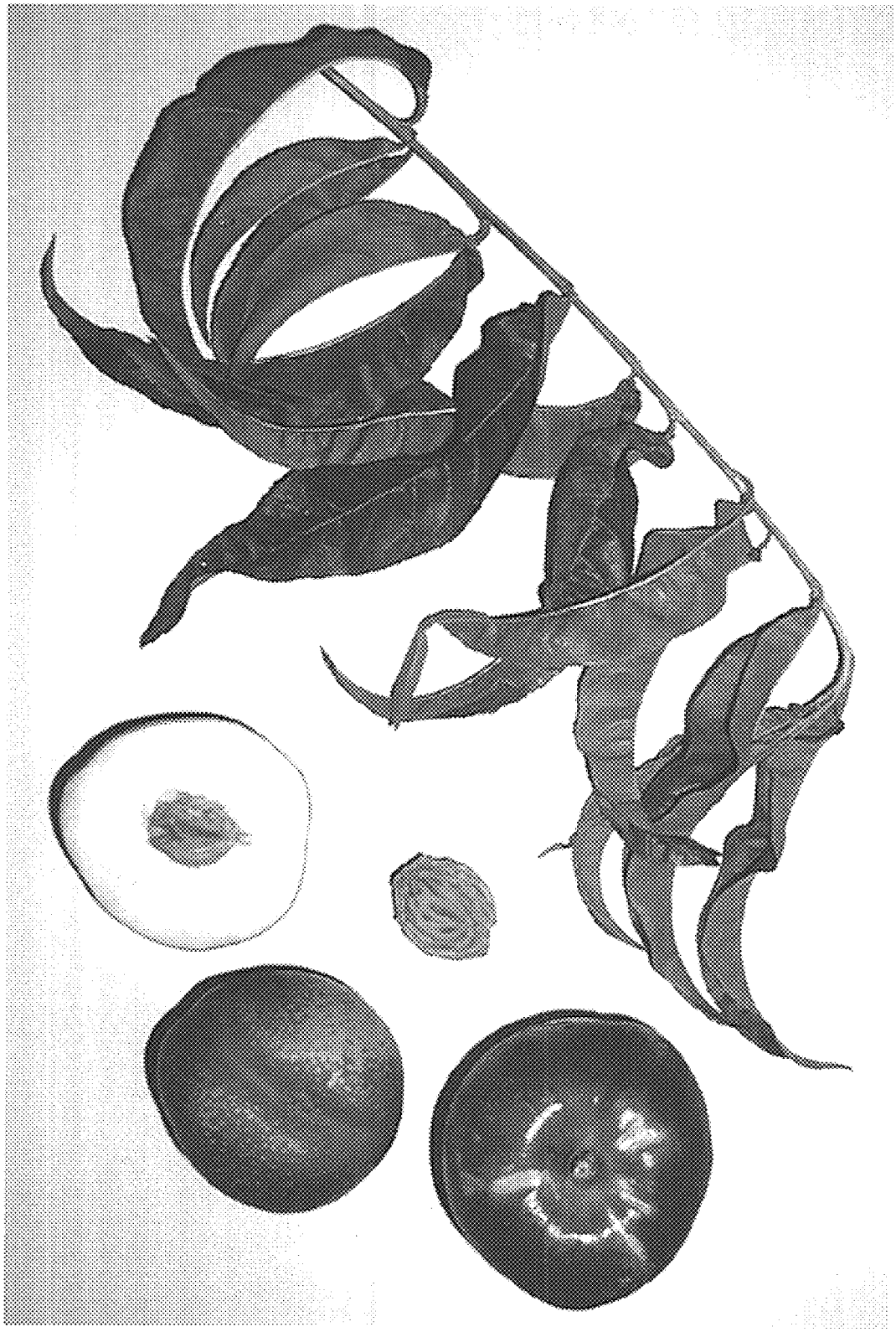

* * * * *